(12) United States Patent
Hoek et al.

(10) Patent No.: US 6,475,943 B1
(45) Date of Patent: Nov. 5, 2002

(54) CATALYST ACTIVATION PROCESS

(75) Inventors: Arend Hoek; Jeroen Harrie Moors, both of Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 09/150,481

(22) Filed: Sep. 9, 1998

Related U.S. Application Data

(63) Continuation-in-part of application No. 08/748,303, filed on Nov. 13, 1996, now abandoned, which is a continuation-in-part of application No. 08/697,304, filed on Aug. 22, 1996, now abandoned.

(30) Foreign Application Priority Data

Nov. 8, 1995 (EP) .............................................. 95203040

(51) Int. Cl.[7] .............................. B01J 38/10; B01J 38/56
(52) U.S. Cl. .............................. 502/53; 502/31; 502/34; 502/325; 502/344; 518/709
(58) Field of Search .............................. 502/34, 53, 31, 502/56, 325, 344; 518/709; 585/906

(56) References Cited

U.S. PATENT DOCUMENTS

| | | | |
|---|---|---|---|
| 4,568,698 A | * | 2/1986 | Desmond et al. |
| 5,073,661 A | * | 12/1991 | Scheffer et al. |
| 5,260,239 A | * | 11/1993 | Hsia |
| 5,283,216 A | * | 2/1994 | Mitchell |
| 5,958,985 A | * | 9/1999 | Geerlings et al. |
| 5,981,608 A | * | 11/1999 | Geerlings et al. |
| 6,130,184 A | * | 10/2000 | Geerlings et al. |

FOREIGN PATENT DOCUMENTS

| | | | |
|---|---|---|---|
| EP | 0 589 692 | * | 3/1994 |
| EP | 0 590 882 | * | 6/1994 |

* cited by examiner

*Primary Examiner*—Steven P. Griffin
*Assistant Examiner*—Christina Ildebrando

(57) ABSTRACT

The present invention relates to a process for the activation of a catalyst in the presence of a hydrocarbon liquid, which catalyst comprises a Group Ib, VIIb or VIII metal compound, by contacting the catalyst with a hydrogen-containing gas at a hydrogen partial pressure of at least 15 bar abs. The present invention further relates to a hydrocarbon synthesis process which comprises activating a hydrocarbon synthesis catalyst in the presence of a hydrocarbon liquid by contacting the catalyst with a hydrogen-containing gas at a hydrogen partial pressure of at least 15 bar abs., and, subsequently, contacting the catalyst with a mixture of hydrogen and carbon monoxide at hydrocarbon synthesis reaction conditions.

7 Claims, 3 Drawing Sheets

US 6,475,943 B1

CATALYST ACTIVATION PROCESS

This is a continuation-in-part of Ser. No. 08/748,303 filed Nov. 13, 1996 now abandoned, which is a continuation-in-part of application Ser. No. 08/697,304 filed Aug. 22, 1996 (now abandoned which claims priority of European Patent Application No. 95203040,1 filed Nov. 8, 1995., the entire disclosure of which is hereby incorporated by reference.

FIELD OF THE INVENTION

The present invention relates to a process for the activation of a catalyst. In particular, the present invention relates to a process for the activation of a hydrocarbon synthesis catalyst, with a hydrogen-containing gas, in the presence of a hydrocarbon liquid.

BACKGROUND

Hydrocarbon synthesis catalysts, that is catalysts capable of catalyzing synthesis of hydrocarbons from hydrogen and carbon monoxide (e.g. Fischer-Tropsch synthesis), typically comprise a Group VIII metal, supported on a catalyst carrier. The Group VIII metal is preferably chosen from iron, nickel, cobalt and/or ruthenium, more preferably iron or cobalt, especially cobalt. The catalyst carrier is preferably an inorganic refractory oxide, more preferably alumina, silica, titania, zirconia or mixtures thereof.

The Group VIII metal which is typically present in the hydrocarbon synthesis catalyst, in particular catalysts comprising iron, cobalt, nickel and/or ruthenium, should at least partly be in the metallic state in order to be active in catalyzing the synthesis of hydrocarbons from carbon monoxide and hydrogen. Thus, prior to use, the catalyst is subjected to one or more reduction, activation, step(s) in the presence of hydrogen.

Various ways to activate hydrocarbon synthesis catalysts are known in the art. Thus, European patent application publication No. 0 533 227 describes a process for the activation of a Fischer-Tropsch catalyst by contact with a hydrogen-containing gas, wherein the hydrogen concentration and the space velocity of the gas increase step-wise or continuously during the activation. European patent application publication No. 0 533 228 describes a process for the activation of a Fischer-Tropsch catalyst, which process comprises contacting the catalyst with a hydrogen-containing gas in a first stage at a total pressure up to 5 bar, rapidly increasing the pressure to at least 10 bar and contacting the catalyst with a hydrogen-containing gas in a second stage at this pressure. U.S. Pat. No. 4,670,414 describes an activation procedure comprising the steps, in sequence, of (a) reduction with a hydrogen-containing gas, (b) oxidation with an oxygen-containing gas, and (c) reduction with a hydrogen-containing gas.

The process for activating hydrocarbon synthesis catalysts may be performed ex-situ, but can also be performed in-situ in the reactor just prior to start-up, particularly for fixed bed units.

Hydrocarbon synthesis processes may be carried out in a number of catalyst bed types, such as fluidized beds, fixed beds, moving beds, ebullating beds and slurry beds. In ebullating and slurry beds in operation, the catalyst is kept dispersed in a liquid, typically a hydrocarbon liquid. Reactant gas bubbles (hydrogen and carbon monoxide) flow upwardly (usually) or downwardly through the catalyst-containing liquid.

It will be appreciated that it would be desirable to be able to activate the catalyst in the presence of the hydrocarbon liquid. This would in particular be desirable for slurry and ebullating catalyst beds. A major problem, however, is the occurrence of hydrogenolysis of the hydrocarbon liquid, which is catalyzed by the (partly) activated hydrocarbon synthesis catalyst. Hydrogenolysis of the hydrocarbon liquid may result in undesired methane formation and adiabatic temperature increase. Further, coke may form, affecting catalyst life and activity. The problem of hydrogenolysis especially applies to hydrocarbon synthesis catalysts comprising more than one metal. For instance, from U.S. Pat. No. 4,588,708 it appears that CO/Mn catalysts are about 15 times more active in the hydrogenolysis reaction than catalyst comprising cobalt only.

U.S. Pat. No. 5,292,705 discloses a process of activating a hydrocarbon synthesis catalyst, wherein the catalyst is first reduced (activated) ex-situ, without hydrocarbon liquids being present, and then the reduced catalyst is subsequently further activated in the presence of hydrogen and a hydrocarbon liquid. It is outlined in column 3, lines 15–23 of that publication that hydrogenolysis and coke formation is avoided in view of the relatively short treatment time.

European patent application publication No. 0 590 882 discloses a similar process in which a partly deactivated, but still reduced, catalyst is subjected to a rejuvenation treatment in the presence of a hydrocarbon liquid.

"Activation," as used herein, is a process in which fresh catalyst is treated with hydrogen to reduce (oxidic) metal compounds to catalytically active metals, thereby activating the catalyst. Therefore, "fresh," as used herein, refers to an unreduced or not yet reduced, oxygenate pre-catalyst which is not yet active. Usually, the catalyst is calcined by reaction with an oxygen containing gas at elevated temperatures before reduction.

"Rejuvenation," as used herein, is a process in which spent catalyst is treated with hydrogen to restore at least part of the initial activity of an activated fresh catalyst. Therefore, "spent," as used herein, refers to a catalyst which is no longer active and which the metals have reverted to their oxidic, pre-catalyst state. Without wishing to be bound by a particular theory, it would appear that, inter alia, the processes which occur during rejuvenation are coke precursor removal, removal of metal-carrier compounds and reduction of metal compounds.

It would be desirable to be able to fully activate or rejuvenate catalyst, in particular a hydrocarbon synthesis catalyst, in the presence of a hydrocarbon liquid, whilst avoiding hydrogenolysis and/or coke formation, and obviating the need of a pre-reduction step.

It has now surprisingly been found possible to activate or rejuvenate catalysts in the presence of a hydrocarbon liquid, by contacting the catalysts with hydrogen or a hydrogen-containing gas in which the hydrogen partial pressure exceeds a certain limit.

SUMMARY OF THE INVENTION

The present invention relates to a process for the activation of a catalyst, preferably a hydrocarbon synthesis catalyst, in the presence of a hydrocarbon liquid which catalyst comprises a Group Ib, VIIb or VIII metal compound, by contacting a fresh or spent catalyst with a hydrogen-containing gas at a hydrogen partial pressure of at least 15 bar abs.

DETAILED DESCRIPTION

Figure 1:
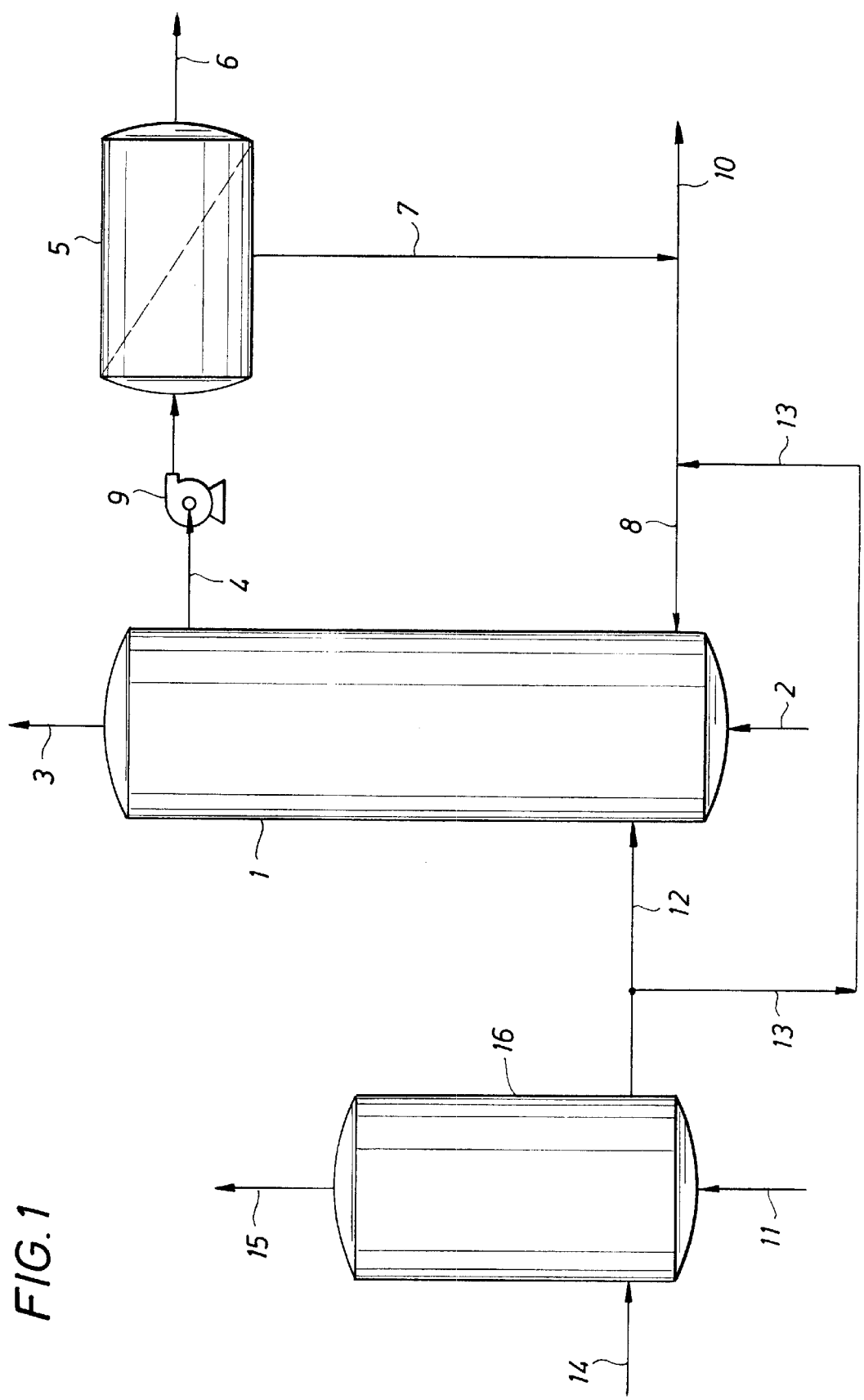
FIG. 1 schematically depicts an embodiment in which the catalyst is activated and/or rejuvenated in-situ in a reactor vessel comprising a slurry or ebullating catalyst bed.

For the purpose of this specification, a hydrogen-containing gas is a gas containing hydrogen and, optionally, one or more inert gas components like nitrogen. A synthesis gas mixture, comprising hydrogen and (substantial amounts of) carbon monoxide, is not included in the term hydrogen-containing gas as used herein.

Preferably, the hydrogen partial pressure is at least 20 bar abs., more preferably at least 30 bar abs. Typically, the hydrogen partial pressure is at most 200 bar abs., preferably at most 100 bar abs. Most preferably, the hydrogen partial pressure is kept in the range from 50 to 60 bar abs.

A preferred catalyst to be activated or rejuvenated according to the process of the present invention comprises a Group VIII metal compound. The term "metal compound" as used herein includes beside metal oxides, hydroxides, carbides, etc.; also the metal itself, especially in the case of rejuvenation. Preferably the metal compound is a cobalt, nickel or ruthenium metal compound or mixtures thereof. Most preferably, the catalyst comprises a cobalt metal compound, in particular a cobalt oxide. The preferred catalyst to be activated or rejuvenated is typically a hydrocarbon synthesis catalyst.

The metal compound is typically supported on a catalyst carrier. A suitable catalyst carrier may be chosen from the group of refractory oxides, preferably, alumina, silica, titania, zirconia, or mixtures thereof; more preferably, silica, titania, zirconia, or mixtures thereof.

"Metal" as used herein means the metal which will be catalytically active following reduction. The metal may be applied to the carrier by any of the techniques known in the art, for example comulling, impregnation, spray-coating or precipitation, especially comulling, impregnation or spray-coating. Impregnation is a particularly preferred technique in which the carrier is contacted with a compound of the metal in the presence of a liquid, most conveniently in the form of a solution of the metal compound. The compound of the metal may be inorganic or organic, with inorganic compounds being preferred, in particular nitrates. The liquid employed may also be either organic or inorganic. Water is a most convenient liquid. It will be appreciated that the water may, at least partly, be derived from crystal water which is liberated from the metal compound upon impregnation at elevated temperature.

The amount of metal present on the carrier is typically in the range of from 1 to 100 parts by weight, preferably 10 to 50 parts by weight, per 100 parts by weight of carrier material.

The metal may be present in the catalyst together with one or more metal promoters or co-catalysts. The promoters may be present as metals or as the metal oxide, depending upon the particular promoter concerned. Suitable promoters include oxides of metals from Groups IIA, IIIB, IVB, VB, VIB and/or VIIB of the Periodic Table, oxides of the lanthanides and/or the actinides. Preferably, the catalyst comprises at least one oxide of an element in Group IVB, VB and/or VIIB of the Periodic Table, in particular titanium, zirconium, manganese and/or vanadium. As an alternative or in addition to the metal oxide promoter, the catalyst may comprise a metal promoter selected from Groups VIIB and/or VIII of the Periodic Table. Preferred metal promoters include rhenium, platinum and palladium.

A most suitable catalyst comprises cobalt as the metal and zirconium as a promoter. Another most suitable catalyst comprises cobalt as metal and manganese and/or vanadium as a promoter. The promoter may be incorporated in the catalyst using any of the methods discussed herein before with respect to the metal component.

The promoter, if present in the catalyst, is typically present in an amount of from 0.1 to 60 parts by weight, preferably from 0.5 to 40 parts by weight, per 100 parts by weight of carrier material. It will however be appreciated that the optimum amount of promoter may vary for the respective elements which act as promoter. If the catalyst comprises cobalt metal and manganese and/or vanadium as promoter, the cobalt: (manganese+vanadium) atomic ratio is advantageously at least 12:1.

The hydrocarbon liquid to be used in the process of the present invention is most suitably a product of a hydrocarbon synthesis process, in particular a process as described herein. Alternatively, (refined) crude oil fractions or liquid polyolefins may be used. Preferably, the hydrocarbon liquid is highly paraffinic. Typically, a highly paraffinic hydrocarbon liquid contains at least 70% by weight, preferably 80% by weight, and more preferably 90% by weight of paraffinic hydrocarbons.

The process is typically carried out at a temperature in the range from 180 to 400° C., preferably from 200 to 350° C., more preferably from 220 to 320° C. A most preferred temperature range, especially for cobalt-containing catalysts, is from 240 to 320° C. For some catalysts containing metal compounds which are difficult to reduce, it may be desirable to operate the process mainly towards the higher end of the range from 180 to 400° C. In such case, it is particularly desirable to operate the process at a high hydrogen partial pressure, typically at least 30 bar abs., preferably at least 50 bar abs. At temperatures below 220° C., especially below 200° C., more especially below 180° C., the partial hydrogen pressure may be lower than the partial hydrogen pressure at which the actual reduction is carried out. At these temperatures hydrogenolysis rates are relatively low, and thus a lower partial hydrogen pressure may be used.

Usually the partial hydrogen pressures will be more than 75% of the final pressure, especially 50% or more, more especially 25% or more for the above indicated temperatures. At temperatures below 180° C., especially below 160° C., the hydrogen partial pressures may be even lower, e.g. 50% or more, especially 25% or more of the final partial hydrogen pressure. Thus, a programmed hydrogen pressure increase/temperature increase profile may be used to reach the final reaction conditions.

During these initial reaction stages already part of the reduction reaction may occur, e.g. up to 40% of the final reduction reaction, preferably up to 20%, more preferably up to 10%.

The activation process according to the present invention is suitably carried out at a constant temperature level or in a programmed way as described above. In a preferred embodiment the activation process is carried out as follows.

Fresh or spent catalyst, in admixture with hydrocarbon liquid, is first heated to an initial temperature, typically in the range from 150 to 180° C. or even 200° C., preferably in the presence of an inert gas like nitrogen. Once this initial temperature is reached, the catalyst is contacted with a hydrogen-containing gas, at the appropriate partial pressure. The temperature is incrementally (step-wise) or continuously increased at a rate in the range from 0.1 to 10° C./min to a final temperature, typically at least 240° C., preferably at least 250° C., but within the temperature ranges as indicated above. It will be understood that if the temperature is increased incrementally, the above temperature increase rate refers to the rate during periods of temperature increase and not to the average temperature increase rate between initial and final temperature.

The mixture of catalyst and hydrocarbon liquid is kept at the final temperature level for a period sufficient to substantially activate the catalyst, typically for at least 0.25 hours, preferably at least 2 hours. If desired, the temperature of the mixture is then incrementally or continuously decreased at a rate in the range from 0.1 to 10° C./min to an end temperature which, for safety reasons, is at least 10° C. lower than the envisaged hydrocarbon synthesis step temperature.

According to one embodiment, the hydrogen-containing gas can then be replaced by a synthesis gas mixture comprising hydrogen and carbon monoxide to start the hydrocarbon synthesis step.

According to another embodiment, the hydrogen-containing gas is first replaced by an inert gas, such as nitrogen, and subsequently, the inert gas is replaced by a synthesis gas mixture to start the hydrocarbon synthesis step. It has been found that in the latter case it is beneficial that the temperature of the mixture of catalyst and hydrocarbon liquid is lower than the temperature at which substantial hydrogenolysis starts to occur, when contacted with the inert gas. Preferably the temperature is lower than 200° C., more preferably, lower than 185° C.

According to a particularly preferred embodiment, the rate of temperature increase is dependent upon the reduction (activation) rate, which can be monitored by the amount of water production. Preferably, the activation is carried out in a controlled way. Thus, the rate of water (steam) production is kept below a certain level. This level may depend on the catalyst being activated and can be determined by routine experimentation. For example catalysts comprising a silica-containing carrier tend to be sensitive to too high quantities of steam present during activation. Thus, if a catalyst is to be activated comprising a silica-containing carrier, the quantity of steam present in the hydrogen-containing offgas is preferably less than 4000 ppmv, more preferably less than 3000 ppmv. For titania- or zirconia-containing catalysts, the quantity of steam in the hydrogen-containing offgas may suitably be higher, for example in the range from 0.4 to 10% by volume. For the latter catalysts it may even be desirable to add additional steam during the activation step.

Suitably, the rejuvenation process is carried out using the same temperature program as typically applied during the activation step. However, it will be appreciated that in the rejuvenation process the spent catalyst is normally already at elevated temperature, typically between hydrocarbon synthesis temperature and an up to 100° C. lower temperature. Thus, a temperature increase program may not be necessary.

The rejuvenation step may be carried out batch-wise or continuously. In a batch-wise mode of operation normally the complete catalyst inventory of a hydrocarbon synthesis reactor vessel is subjected to a rejuvenation treatment. Preferably, the rejuvenation treatment is carried out in-situ. The hydrocarbon synthesis process is temporarily stopped by interrupting the synthesis gas supply, and introducing hydrogen-containing gas into the reactor. In a continuous mode of operation, a small portion of catalyst is withdrawn from the hydrocarbon synthesis reactor and rejuvenated in a separate rejuvenation vessel. It will be appreciated that it is also possible to withdraw portions of catalyst in a batch-wise mode of operation.

The rejuvenation step is preferably carried out at a temperature range which is from 50° C. below the hydrocarbon synthesis operating temperature to 50° C. above the hydrocarbon synthesis temperature, but still within the broad temperature range as indicated above.

The temperature can be incrementally or continuously increased or decreased to the desired rejuvenation temperature at a rate in the range from 0.5 to 20° C./min. The temperature is kept at the desired rejuvenation temperature level for a period sufficient to substantially rejuvenate the catalyst, typically for at least 10 minutes, preferably at least 30 minutes, more preferably at least 1 hour.

If desired, the temperature is then incrementally or continuously decreased or increased to the desired end temperature at a rate in the range from 0.5 to 20° C./min, which for safety reasons, is at least 10° C. lower than the envisaged hydrocarbon synthesis step temperature.

It will be appreciated that the synthesis gas supply to the catalyst to be rejuvenated may simply be replaced by a hydrogen-containing gas, and the hydrogen-containing gas may simply be replaced by a supply of synthesis gas, following the rejuvenation step. It may, however, be desired to replace the synthesis gas and/or the hydrogen-containing gas supply as the case may be, first with a supply of an inert gas such as nitrogen, followed by replacing the inert gas with hydrogen-containing gas or synthesis gas. In that case, it is beneficial that the temperature of the mixture of catalyst and hydrocarbon liquid is lower than the temperature at which substantial hydrogenolysis starts to occur in the presence of the inert gas. Preferably the temperature is lower than 200° C., more preferably, lower than 185° C.

The volume percentage of hydrogen present in the hydrogen-containing gas may vary between wide limits. Typically, a hydrogen-containing gas is employed comprising from 25 to 100% by volume of hydrogen. For economic reasons, the hydrogen-containing gas preferably comprises from 50 to 100% by volume of hydrogen, more preferably 80 to 100% by volume of hydrogen.

The hydrogen-containing gas may be derived from known sources. Suitable examples include a dedicated hydrogen manufacturing facility and a tail gas from a hydrocarbon synthesis process. The tail gas to be used in the activation and rejuvenation process typically comprises hydrogen, carbon dioxide, carbon monoxide, gaseous hydrocarbon products and water. Optionally, the tail gas is treated to remove gaseous hydrocarbon products, carbon dioxide and/or water. The amount of carbon monoxide should be less than 5% by volume, preferably, less than 2% by volume. If the tail gas contains more carbon monoxide, the tail gas is first led to a means capable of separating a hydrogen-rich, carbon monoxide-depleted gas from the tail gas. An example of such means is a Pressure Swing Adsorber.

The process is typically carried out for a period sufficient to activate or rejuvenate the catalyst. It will be appreciated that this period may vary, depending on the composition of the catalyst, the average reaction temperature and hydrogen partial pressure. Typically, the catalyst is contacted with the hydrogen-containing gas for 0.5 to 48 hours, preferably for 6 to 36 hours.

According to a preferred embodiment, the catalyst is contacted with the hydrogen-containing gas until at least 25% by weight, preferably at least 50% by weight, more preferably at least 80% by weight, of the metal compound is reduced to the metallic state.

The quantity of the metal compound that has been reduced, can suitably be monitored by measurement of cumulative water production during the process. Other methods known to those skilled in the art include Thermogravimetric Analysis and Temperature Programmed Reduction.

The activation and rejuvenation process in the presence of hydrocarbon liquids is especially advantageous for use in hydrocarbon synthesis processes which operate with ebullating or slurry catalyst beds.

Ebullating and slurry catalyst beds are well known to those skilled in the art. In ebullating and slurry beds in operation, the catalyst is kept dispersed in a liquid, typically a hydrocarbon liquid. Reactant gas bubbles (hydrogen and carbon monoxide) flow (usually) upwardly through the catalyst-containing liquid.

According to a preferred embodiment, in the process for activation/rejuvenation of slurry or ebullating bed catalyst, the catalyst is kept dispersed in the hydrocarbon liquid. The process is exothermic. By keeping the catalyst dispersed in the liquid, heat transfer is facilitated.

The catalyst can be kept dispersed in the hydrocarbon liquid by maintaining a high upward superficial velocity of the hydrocarbon liquid, and/or by injection of hydrogen-containing gas at a sufficiently high superficial gas velocity.

It may be preferred to operate with a low liquid velocity along the slurry bubble column, that is a low superficial velocity of the hydrocarbon liquid, as this may reduce or obviate the need for a liquid, slurry, recycle. This may reduce the complexity of operating procedures of the reactor and may reduce operating and capital expenditure.

It may also be preferred, however, to operate with a high liquid velocity along the slurry bubble column. This may be the case if it is desired to separate liquid product and catalyst outside the reactor, or, for example, if it is desired to continuously rejuvenate the catalyst in a separate vessel.

It has been found especially advantageous for catalysts comprising silica to activate the catalyst in-situ in the reactor vessel.

Typically, the superficial liquid velocity is kept in the range from 0.05 to 4.0 cm/sec. It will be appreciated that the preferred range may depend on the preferred mode of operation, as discussed above.

If it is desired to operate at a low superficial liquid velocity, the velocity is preferably kept in the range from 0.05 up to 1.0 cm/sec, more preferably from 0.2 to 0.8 cm/sec.

If it is desired to operate at a high superficial liquid velocity, the velocity is preferably kept in the range from 0.5 to 4.0 cm/sec, depending inter alia on the size and density of the catalyst particles, more preferably from 1.0 to 3.0 cm/sec.

Typically, the superficial gas velocity of the hydrogen-containing gas ranges from 0.5 to 50 cm/sec, preferably from 0.5 to 0 cm/sec, more preferably from 1 to 30 cm/sec, still more preferably from 1 to 15 cm/sec.

According to a further aspect, the present invention relates to a hydrocarbon synthesis process which comprises activating or rejuvenating a hydrocarbon synthesis catalyst in the presence of a hydrocarbon liquid by contacting the catalyst with a hydrogen-containing gas at a hydrogen partial pressure of at least 15 bar abs., and, subsequently, contacting the catalyst with a mixture of hydrogen and carbon monoxide at hydrocarbon synthesis reaction conditions.

The hydrocarbon synthesis process is typically carried out at a temperature in the range from 125 to 350° C., preferably 200 to 275° C. The pressure typically ranges from 5 to 80 bar abs., preferably from 20 to 60 bar abs.

Hydrogen and carbon monoxide (synthesis gas) is typically fed to the process at a molar ratio in the range from 0.4 to 2.5. It is known that especially low hydrogen to carbon monoxide molar ratios will increase the $C_{5+}$ selectivity of Fischer-Tropsch catalysts. However, as the ratio in which the synthesis gas is normally consumed is about 2, expensive recycles have to be applied if synthesis gas having a low hydrogen to carbon monoxide molar ratio is fed to the process, and the catalyst to be applied does not have water gas shift activity. In a preferred embodiment of the hydrocarbon synthesis process, the hydrogen to carbon monoxide molar ratio is in the range from 1.0 to 2.5, especially 1.5 to 2.5.

The gas hourly space velocity may vary within wide ranges and is typically in the range from 400 to $14000h^{-1}$, e.g. 400 to $4000h^{-1}$.

The process for the preparation of hydrocarbons may be conducted using a variety of reactor types and reaction regimes, for example a fixed bed regime, a slurry phase regime or an ebullating bed regime. It will be appreciated that the size of the catalyst particles may vary depending on the reaction regime they are intended for. It belongs to the skill of the skilled person to select the most appropriate catalyst particle size for a given reaction regime.

Further, it will be understood that the skilled person is capable to select the most appropriate conditions for a specific reactor configuration and reaction regime. For example, the preferred gas hourly space velocity may depend upon the type of reaction regime that is being applied. Thus, if it is desired to operate the hydrocarbon synthesis process with a fixed bed regime, preferably the gas hourly space velocity is chosen in the range from 500 to 2500 Nl/l/h. If it is desired to operate the hydrocarbon synthesis process with a slurry phase regime, preferably the gas hourly space velocity is chosen in the range from 1500 to 8000 $h^{-1}$, especially from 3000 to 3500 $h^{-1}$.

Preferably, the hydrocarbon synthesis step is carried out in an ebullating or slurry catalyst bed in the presence of a hydrocarbon liquid. At least during the hydrocarbon synthesis step, the catalyst is kept dispersed in the hydrocarbon liquid. Preferably, the catalyst is kept dispersed during the activation or rejuvenation step and during the hydrocarbon synthesis step.

Preferably, the superficial gas velocity of the synthesis gas is in the range from 0.5 to 50 cm/sec, more preferably in the range from 5 to 35 cm/sec.

Typically, the superficial liquid velocity is kept in the range from 0.05 to 4.0 cm/sec. It will be appreciated that the preferred range may depend on the preferred mode of operation, as discussed above with respect to the activation/rejuvenation step.

If it is desired to operate at a low superficial liquid velocity, the velocity is preferably kept in the range from 0.05 up to 1.0 cm/sec, more preferably from 0.2 to 0.8 cm/sec.

If it is desired to operate at a high superficial liquid velocity, the velocity is preferably kept in the range from 0.5 to 4.0 cm/sec, depending inter alia on the size and density of the catalyst particles, more preferably from 1.0 to 3.0 cm/sec.

According to one embodiment of the invention, the activation and/or rejuvenation and hydrocarbon synthesis steps are carried out in the same reactor vessel, more preferably in the same catalyst bed.

According to another embodiment of the invention, the activation and/or rejuvenation and hydrocarbon synthesis steps are carried out in separate vessels, that is a reactor vessel for the hydrocarbon synthesis step and a combined activation/rejuvenation vessel, or separate activation and rejuvenation vessels.

Thus, catalyst to be rejuvenated is led, together with hydrocarbon liquid, to the activation/rejuvenation vessel or rejuvenation vessel, from the hydrocarbon synthesis vessel, and rejuvenated catalyst, together with hydrocarbon liquid is led back to the hydrocarbon synthesis vessel.

Fresh or spent catalyst to be activated is introduced into the activation/rejuvenation vessel or the activation vessel, and activated catalyst is led with hydrocarbon liquid to the hydrocarbon synthesis vessel. Preferably, the hydrocarbon liquid comprises a product of the hydrocarbon synthesis step.

According to one embodiment of the invention, the activation/rejuvenation or rejuvenation step is combined with a hydrogenation step in which hydrocarbon liquid is hydrogenated and hydrogenated product is obtained.

Embodiments of the invention will now be described in more detail with reference to FIGS. 1 to 3. It will, however, be readily appreciated by those skilled in the art that various alternative embodiments are possible, without departing from the scope of the invention.

With reference to FIG. 1, a reactor vessel 1, comprising a slurry or ebullating bed of catalyst and cooling means (not shown) is equipped with gas inlet means 2 and gas outlet means 3. The fresh or spent catalyst present in the reactor vessel may now be activated or rejuvenated by introducing a hydrogen-containing gas at appropriate conditions into reactor vessel 1 via gas inlet means 2. A gaseous effluent, comprising unconverted hydrogen, inert gases and steam, leaves the reactor vessel via as outlet means 3.

Following activation or rejuvenation of the catalyst, synthesis gas, is introduced into reactor vessel 1 via gas inlet means 2. Due to the high exothermicity of the hydrocarbon synthesis reaction, the slurry or ebullating catalyst bed is preferably at a temperature lower than the envisaged reaction temperature, more preferably at least 10° C. below the envisaged reaction temperature before synthesis gas is introduced into the reactor vessel 1.

A catalyst slurry comprising hydrocarbon product is led through line 4 and pump 9 to separation means 5. Catalyst-free hydrocarbon product is discharged through line 6, and a concentrated catalyst slurry is led from separation means 5, through lines 7 and 8 back to reactor vessel 1.

Spent catalyst can be discharged through line 10 and, if desired, can be regenerated or rejuvenated in means not shown or rejuvenated in activation vessel 16, to be discussed hereinafter, and thereafter led back to reactor vessel 1.

If desired, part or all of the separation means 5 may be integrated into the reactor vessel 1. Further, line 10 may be omitted if the reactor vessel further comprises a catalyst outlet means. This is particularly desired if separation means 5 is integrated into reactor vessel 1.

In a preferred embodiment, fresh catalyst which has been activated is introduced into reactor vessel 1 from separate activation vessel 16. Activation vessel 16 comprises gas inlet means 11, catalyst inlet means 14 and gas outlet means 15. Activated catalyst is led via line 12 or via line 13 and 8 into reactor vessel 1. Activation in vessel 16 is typically carried out in the presence of hydrocarbon liquid, which can be derived from line 6 and introduced into vessel 16 together with fresh catalyst via catalyst inlet means 14.

It will be appreciated that in an alternative embodiment, reactor vessel 1 is not used for activation or rejuvenation of the catalyst but is continuously used for hydrocarbon synthesis. Like in the embodiment discussed above, fresh catalyst is activated in activation vessel 16 and introduced into reactor vessel 1 via lines 12 or 13 and 8, and spent catalyst is discharged through line 10. It will be appreciated that upon start-up, fresh catalyst is activated in batches in activation vessel 16. Activated catalyst batches may then be introduced into the reactor vessel where the catalyst is kept under conditions which avoid coke formation and/or hydrogenolysis, that is at a low temperature, preferably below 185° C., and/or in the presence of a hydrogen-containing as at a hydrogen-partial pressure of at least 15 bar abs., preferably at least 20 or at least 30 bar abs.

Figure 2:
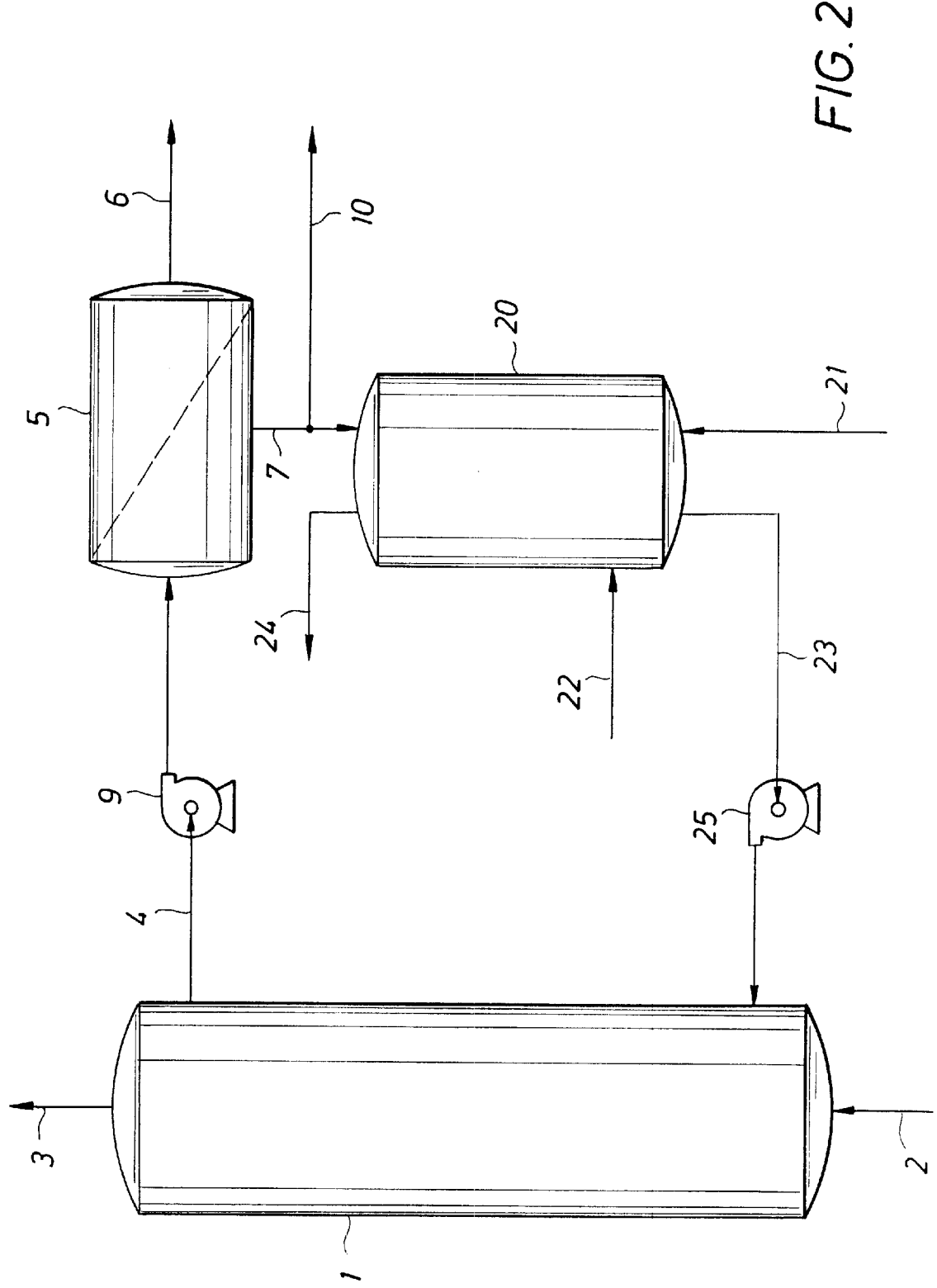
FIG. 2 schematically depicts an embodiment in which a concentrated catalyst slurry is activated and rejuvenated.
Figure 3:
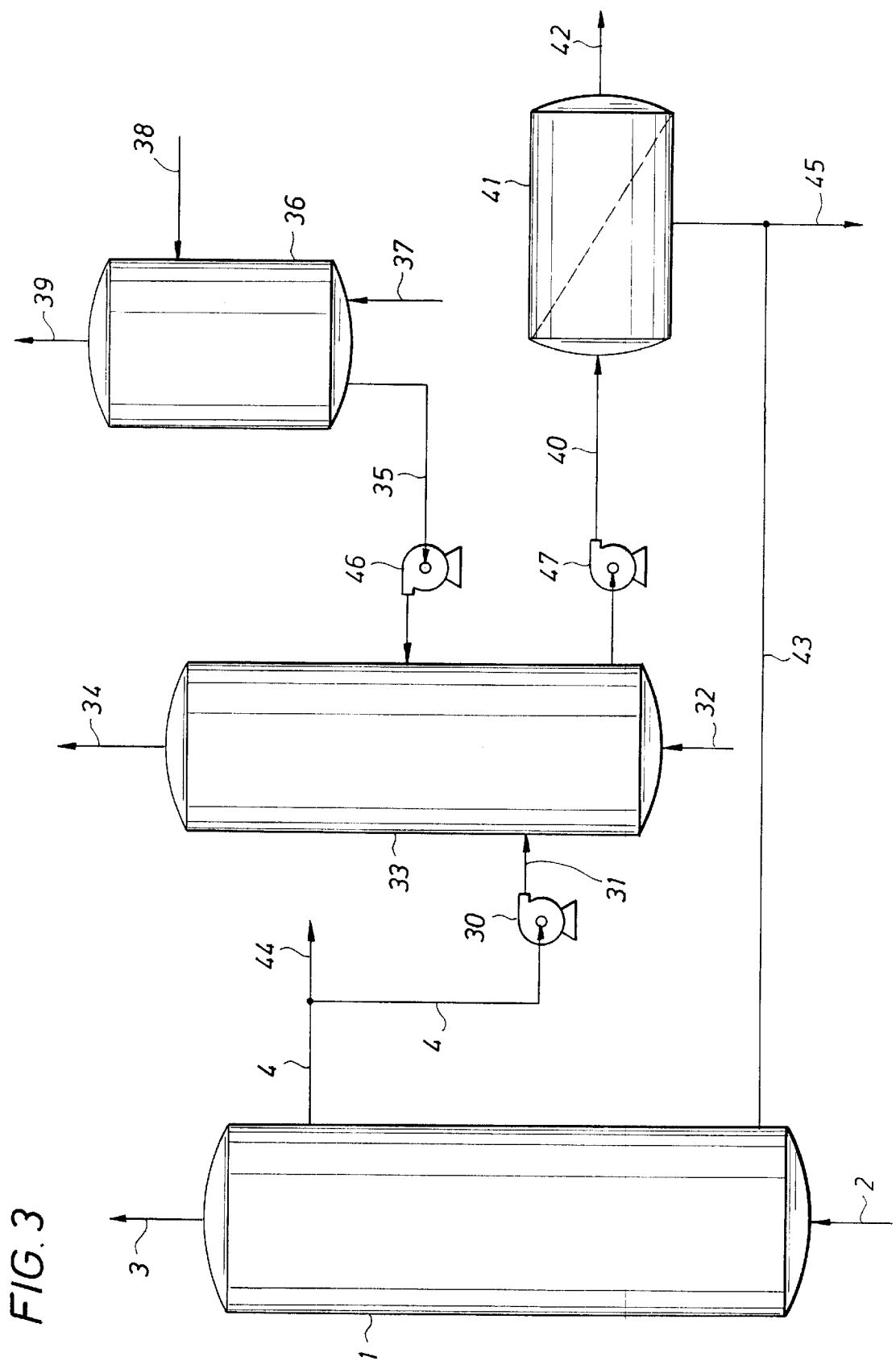
FIG. 3 schematically depicts an embodiment in which at least a part of a catalyst slurry together with hydrocarbon-containing product is led to a hydrogenation reactor to simultaneously hydrogenate the hydrocarbon-containing product and to rejuvenate the catalyst.

With reference to FIG. 2 and 3, reference numbers which correspond with numbers in FIG. 1, have the same meaning as in FIG. 1.

It will be readily appreciated by those skilled in the art that preferred or alternative embodiments discussed in relation to FIG. 1 may, where appropriate, be applied in the process line-up schematically depicted in either of FIGS. 2 or 3 or in further alternative process line-ups.

FIG. 2 schematically depicts an embodiment in which at least part of a concentrated catalyst slurry in line 7 is led to a rejuvenation vessel 20. A hydrogen-containing gas is introduced into vessel 20 via line 21. Optionally, catalyst which may have been partly or fully activated in means not shown, is introduced into vessel 20 via line 22. A rejuvenated catalyst slurry is led through line 23 and pump 25 to reactor vessel 1. A gaseous effluent, comprising unconverted hydrogen, inert gases and steam, leaves the vessel 20 via gas outlet means 24.

Alternatively, pump 25 is omitted and the concentrated catalyst slurry of higher density than the catalyst slurry in reactor vessel 1, is led back into the reactor vessel by gravity.

FIG. 3 schematically depicts an embodiment in which at least part of a slurry of catalyst and hydrocarbon-containing product is led through line 4, pump 30 and line 31 to a hydrogenation reactor 33 to simultaneously hydrogenate the hydrocarbon-containing product and to rejuvenate the catalyst. Hydrogen-containing gas is introduced in reactor 33 via line 32. Gaseous effluent leaves the reactor 33 via line 34.

Optionally, the reactor 33 is also used to simultaneously activate fresh catalyst, which is introduced into reactor 33 as make-up for any withdrawn spent catalyst. The fresh catalyst is kept in vessel 36, which is equipped with catalyst slurry inlet means 38, and optionally with gas inlet means 37 and outlet means 39 to enable at least partly pre-reducing the catalyst prior to introduction into vessel 33. Fresh or optionally partly or fully activated catalyst is led from vessel 36 through line 35 and pump 46 to vessel 33. It will be appreciated that according to an alternative embodiment, fully activated catalyst from vessel 36 is led directly to slurry bubble column via means not shown.

The slurry effluent from reactor 33 comprising rejuvenated catalyst and hydrogenated hydrocarbon-containing product is led via line 40 and pump 47 to separation means 41. Hydrogenated hydrocarbon-containing product leaves the separation means 41 via line 42. A concentrated rejuvenated catalyst slurry is led to reactor vessel 1 via line 43.

Spent catalyst can suitably be withdrawn from the recycle via lines 44 or 45.

The invention will now be described further by means of the following Examples.

EXAMPLE I

The following experiments demonstrate the effect of hydrogen partial pressure on hydrogenolysis activity of a fully activated catalyst comprising 22% by weight of cobalt on a zirconia-silica carrier.

In the experiments, a microflow unit was loaded with 9.5 ml of fresh catalyst. The fresh catalyst was activated in the absence of hydrocarbons at a temperature of 290° C. and a hydrogen partial pressure of 3 bar.

Subsequently, n-hexadecane was led through the catalyst bed at elevated temperature and in the presence of hydrogen. Hydrogenolysis activity was determined by measuring the amount of methane in the offgas. Results are summarized in Table I.

As can be seen in Table I, the hydrogenolysis activity at high hydrogen partial pressures is much lower than the activity at lower hydrogen partial pressures.

TABLE I

| No. | 1 | 2 | 3 | 4 | 5 | 6 |
|---|---|---|---|---|---|---|
| T(° C.) | 255 | 273 | 260 | 270 | 250 | 274 |
| n-$C_{16}$ | 3.1 | 3.1 | 3.2 | 3.4 | 3.4 | 3.4 |
| GHSV | 1.7 | 1.7 | 1.7 | 1.2 | 1.2 | 1.2 |
| p($H_2$) | 29.0 | 29.5 | 11.3 | 7.0 | 38.7 | 38.9 |
| $CH_4$ | 0.6 | 2.0 | 4.6 | 12.6 | 0.3 | 1.5 |

Legend:
n-$C_{16}$= n-hexadecane flow in g/l
GHSV= Gas Hourly Space Velocity in $Nm^3/l/h$.
p($H_2$)= Hydrogen paitial pressure in barg
$CH_4$= $CH_4$ production in mmol/h

EXAMPLE II

A fresh cobalt on zirconia-silica catalyst, having an average particle size of about 40 μm, was activated in-situ in a slurry bubble column of 10 cm diameter in the presence of a hydrocarbon liquid. The slurry of hydrocarbon liquid and catalyst contained 30% by volume of catalyst.

The fresh catalyst was suspended in a commercially available start-up hydrocarbon oil, marketed by Shell Companies under the tradename ONDINA-68, and dried under nitrogen at 3 bar abs. and a superficial gas velocity Ug of 6 cm/sec. The temperature was continuously increased from 20° C. to 180° C. at a rate of 5° C./h.

At 180° C., the slurry bubble column was pressurized to 60 bar abs. and nitrogen was replaced by hydrogen (100% by volume) in once-through operation. The temperature was increased by 5° C./h to 260° C. The catalyst slurry was kept at this temperature for 2 hours. If necessary, the temperature was temporarily kept constant or was decreased to keep the steam concentration in the off-gas below 4000 ppmv.

Hydrogenolysis was monitored by on-line analysis of $CH_4$ in off-gas. At a temperature of 260° C. a maximum $CH_4$ content of 0.05% by volume was observed in the off-gas.

Following activation, the temperature was reduced to 180° C., and the pressure was reduced to 40 bar abs. Synthesis gas was introduced at a superficial gas velocity Ug of 10 cm/sec. The $H_2$/CO ratio at the inlet of the slurry bubble column was 1.1 (v/v). The temperature was increased to 210° C. and the slurry bubble column was allowed to line out for 48 hours. A first order rate constant of 0.11 mol converted CO/kg catalyst/bar $H_2$ was obtained for Fischer-Tropsch synthesis.

For comparative purposes, the same catalyst was activated in the absence of liquid hydrocarbons in a fixed bed microflow unit and tested in gas phase once-through operation to determine its intrinsic activity, that is, excluding any intra-particle mass transfer limitations.

Activation was carried out at 2 bar abs. total pressure, using a hydrogen/nitrogen gas mixture at a GHSV of 2600 N1/1/h and 260° C. The water concentration was kept below 4000 ppmv by varying the hydrogen partial pressure of the gas mixture. After 3 hours, the gas mixture was replaced by 100% hydrogen gas. The catalyst was kept at this condition for 16 hours.

Subsequently, the temperature was lowered to 180° C., and synthesis gas was introduced at 800 N1/1h. The $H_2$/CO ratio at the inlet of the microflow unit was 1.1 (v/v). The temperature was increased to 210° C. and the system was lined out for 48 hrs.

A first order reaction rate constant of 0.10 mol converted CO/kg catalyst/bar $H_2$ was obtained for Fischer-Tropsch synthesis.

Accordingly, the catalyst activated in the presence of hydrocarbon liquid has about the same activity as the catalyst activated in the absence of hydrocarbon liquid.

The hydrogenolysis activity during activation in the presence of hydrocarbon liquid was negligible.

What is claimed is:

1. A process for the activation of a fresh or rejuvenation of a spent catalyst in the presence of a hydrocarbon liquid, which catalyst is a hydrocarbon synthesis catalyst comprising a Group Ib, VIIb or VIII metal compound, said process comprising contacting a fresh or spent catalyst in a reactor with a hydrogen-containing gas at a hydrogen partial pressure of at least 30 bar abs for a time sufficient to activate or rejuvenate said catalyst, wherein said contact further takes place in the presence of a hydrocarbon liquid, which liquid is selected from a product of a hydrocarbon synthesis process crude oil fractions, liquid polyolefins, or mixtures thereof; and subsequently contacting the catalyst with a mixture of hydrogen and carbon monoxide at hydrocarbon synthesis conditions.

2. A process as claimed in claim 1, wherein the hydrogen partial pressure is at least 30 bar abs and at most 200 bar abs.

3. A process as claimed in claim 1, wherein the catalyst comprises a cobalt compound and a carrier selected from the group consisting of alumina, silica, titania, zirconia, and mixtures thereof.

4. A process as claimed in claim 3, wherein during the activation or rejuvenation process the temperature is kept in the range from 180 to 400° C.

5. A process as claimed in claim 4, wherein during the activation or rejuvenation process the superficial gas velocity of the hydrogen-containing gas is from 0.5 to 30 cm/sec and the hydrogen-containing gas is employed comprising from 25 to 100% by volume hydrogen.

6. A process as claimed in claim 5, wherein during the activation or rejuvenation process the fresh or spent catalyst is contacted with the hydrogen or hydrogen-containing gas for 0.5 to 48 hours.

7. A process as claimed in claim 1, wherein the hydrocarbon liquid, which comprises the product of the hydrocarbon synthesis step, is led from the hydrocarbon synthesis step to the activation step, in which step the hydrocarbon liquid is hydrogenated and hydrogenated product is obtained.

* * * * *